United States Patent [19]

Simkin

[11] Patent Number: 4,497,793

[45] Date of Patent: Feb. 5, 1985

[54] MICROENCAPSULATED NATURALLY OCCURING PYRETHRINS

[75] Inventor: Joseph Simkin, Miami, Fla.

[73] Assignee: Pennwalt Corporation, Philadelphia, Pa.

[21] Appl. No.: 470,014

[22] Filed: Feb. 25, 1983

Related U.S. Application Data

[63] Continuation-in-part of Ser. No. 177,213, Aug. 11, 1980, abandoned.

[51] Int. Cl.³ .................. A01N 25/28; A61K 9/52; A61K 9/58; B01J 13/02
[52] U.S. Cl. ............................ 424/32; 264/4.7; 424/19; 428/402.21
[58] Field of Search ............... 264/4.7; 428/402.21; 424/32, 19

[56] References Cited

U.S. PATENT DOCUMENTS

| | | | |
|---|---|---|---|
| 3,270,100 | 8/1966 | Jolkovski et al. | 264/4.7 X |
| 3,429,827 | 2/1969 | Ruus | 264/4.7 X |
| 3,577,515 | 5/1971 | Vandegaer | 424/32 |
| 3,959,464 | 5/1976 | DeSavigny | 424/78 |
| 4,056,610 | 11/1977 | Barber, Jr. et al. | 424/19 X |

OTHER PUBLICATIONS

R. Cremlyn: *Pesticides*, John Wiley & Sons (1978), pp. 39–49.

*Primary Examiner*—Richard D. Lovering

[57] ABSTRACT

A process for microencapsulating naturally-occurring pyrethrins with a polyamide-polyurea shell by interfacial condensation which includes slowly adding an amine reactant to an aqueous emulsion containing the pyrethrin, an isocyanate, and an acyl halide with the requirement that at least one of said isocyanate or said acyl halide is polyfunctional, to provide free flowing capsules having a polyamide-polyurea wall encapsulating the natural pyrethrin.

10 Claims, No Drawings

MICROENCAPSULATED NATURALLY OCCURING PYRETHRINS

CROSS REFERENCE TO RELATED APPLICATIONS

This application is a continuation-in-part of U.S. Ser. No. 177,213, filed Aug. 11, 1980 (now abandoned) and is related to the patent application of Joseph Simkin and Howard Bohm entitled "Entomologically Active Coating Materials for Comestible Packaging" Ser. No. 177,212, filed Aug. 11, 1980, (now abandoned) both of which are incorporated herein by reference.

BACKGROUND OF THE INVENTION

This invention relates to a process for the formulation of microencapsulated insecticides of the pyrethrin family. More particularly, a process for the microencapsulation of natural pyrethrins employing polyamide-polyurea capsule walls is disclosed which is also applicable to the microencapsulation of "synergized" natural pyrethrins. This invention is also concerned with resulting microencapsulated insecticidal materials and with processes for their use.

The pyrethrins are a class of entomologically active materials which are based upon certain chemical species which occur naturally in pyrethrin plants. Pyrethrins, whether naturally occurring or synthetic, have for some time been recognized as being insecticidal agents. A further advantage of pyrethrins as insecticides is their relatively low toxicity towards mammals and to certain other non-insect species. Thus, the pyrethrins as a class are known to be "environmentally acceptable" as insecticides.

A serious drawback to the widespread employment of pyrethrins as insecticides is the fact that they are labile toward oxidation, hydrolysis and other degradation. As a result, the entomological activity of pyrethrins decreases with time; they are, accordingly, known to be relatively non-persistent. While a lack of persistency may be beneficial in certain applications such as for use in the vicinity of domiciles, for many applications, such lack of persistency is a severe drawback. Thus, for example, the use of native pyrethrins in agriculture is generally economically unfeasible due to such lack of persistency. As will be apparent, increasing the persistency of pyrethrin insecticides is a desirable goal; progress toward this goal has been made on several fronts. Thus, certain synthetically-derived pyrethrin insecticides have been formulated which have greater resistance toward degradation and concomitantly longer persistency. Other attempts at increasing the persistency of pyrethrin pesticides have focused on partial isolation of the insecticide from the degrading effects of the environment. Thus, for example, U.S. Pat. No. 4,056,610 issued to Barber, Jr. et al discloses the formulation of microencapsulated insecticides, including pyrethrins, with polyurea microcapsules having photostabilizing ultraviolet light absorbent materials which minimize photoxidation of the encapsulated species. As will be discussed more fully hereinbelow, the traditional methods of microencapsulation such as practiced in U.S. Pat. Nos. 3,577,515 issued to Vandegaer, 3,270,100 issued to Jolkovski, 3,429,827 issued to Ruus, or 3,959,464 issued to DeSavigny, when applied to naturally-occurring pyrethrins, do not provide polyamide-polyurea microencapsulated naturally-occurring pyrethrins acceptable for use in many processes. This invention overcomes this and other shortcomings.

The process of this invention constitutes a modification of known process for the formulation of polyamide-polyurea microencapsulated materials. In this respect, reference is again made to the U.S. Vandegaer and DeSavigny patents, both assigned to the assignee of this invention, both of which patents are incorporated herein by reference. These patents provide an excellent overview of polyamide-polyurea microencapsulation techniques. The Barber patent, U.S. Pat. No. 4,056,610 which discloses an approach toward the microencapsulation of inter alia pyrethrins, is limited to polyurea-type encapsulation systems and is not directed to the polyamide-polyurea systems of the present invention. Accordingly, those skilled in the art are directed to the Vandegaer and DeSavigny patents for a fundamental understanding of interfacial polymerization techniques and methods leading to microencapsulation employing polyamide-polyurea systems.

In general, the microencapsulation technique of Vandegaer and DeSavigny is accomplished by interfacial polymerization. Purusant to this technique, a dispersed phase of a liquid containing the pyrethrin is established in a continuous phase, the dispersed phase further contains the first of at least two complimentary reactants which react together to form the capsule wall by condensation polymerization. Thereafter, the second of the complementary reactants is introduced into the continuous phase and polymerization occurs at the interface between the dispersed droplets and the continuous suspension medium. It will be understood by those skilled in the art that more than two complementary polymer-forming reactants may be incorporated in varying combinations in either of the immiscible liquid phases as long as contact between two complimentary reactants takes place only by mixing.

In general, it is desirable to form microcapsules having capsule walls which are cross-linked. As recognized by Vandegaer, such cross-linking is possible only by including one or more "polyfunctional" species in the polymer system. In this regard, polyfunctional is defined to mean "having at least three reactive functionalities per molecule." Those skilled in the art will appreciate that such reactive functionalities may be the same or different. Such persons will also appreciate that it is not necessary for all of the molecules of a constituent species to have three or more functionalities for such species to be polyfunctional. Thus a species may be said to be polyfunctional when it has in excess of two reactive functionalities on average. For example, polymethylene polyphenylisocyanate may be considered to be polyfunctionaly even though, on average, each molecule may have only about 2.6 reactive functionalities.

It is therefore, necessary for at least one of the aqueous or organic phases to comprise at least one polyfunctional species in order to secure cross-linked capsule walls. Those skilled in the art will understand that the degree of cross-linking may be controlled by control of the amount of polyfunctional species relative to the total polymerizable materials.

The first and second reactive species are chosen so as to be reactive with each other under the conditions prevailing during the reaction. As will be apparent for those skilled in the art from a review of the Vandegaer and DeSavigny patents which have been incorporated herein by reference, many choices exist for such first and second reactive species and may possible polymeric products may result from the reaction thereof. Thus, capsule walls may comprise amide (sulfonamide, etc.), urethane, urea, ester, and many other functions. For the practice of this invention, it has been found necessary to employ polyamide-polyurea systems.

It has been found that the general method of microencapsulation taught by Vandegaer and DeSavigny is relatively ineffective in providing satisfactory microencapsulated insecticidal material from naturally ocurring pyrethrins when use with polyamide-polyurea systems. Thus, the practice of the Vandegaer microencapsulation technique for polyamide-polyurea encapsulation with naturally-occurring pyrethrins yields microencapsulated products having a significant amount to "tackiness". This is manifested by a tendency of such microcapsules to "agglomerate" or to stick together in lumpy assemblages. Agglomeration of microcapsules results in an inability of such capsules to flow freely; a measure of agglomeration is the inability of substantial portions of the capsules to pass a 40 mesh screen. Thus, non-agglomerated capsules will pass a 40 mesh screen to the extent of at least 80% and more preferably 90%. Even more preferably non-agglomerated capsules will pass a 50 mesh screen to the extent of at least about 80%. Such agglomerated microcapsules are unsuitable for use as sprayable formulations especially for agricultural and structural pest control, for coating, and for other uses. While it is not entirely understood what mechanism occurs to cause the establishment of tackiness or agglomeration in such systems, it is believed that the chemical nature of naturally-occurring pyrethrins may be such that interference with the capsule wall polymerization process takes place. Alternatively, it is possible that impurities which are usually associated with naturally-occurring pyrethrins and pyrethrin preparations undertake such interference, resulting in agglomeration upon the practice of such prior microencapsulation techniques. More particularly, it is believed that naturally-occurring pyrethrins or impurities associated therewith may react with amine reactants in microencapsulation systems, thus to result in the observed agglomeration. The Vandegaer and DeSavigny patents both disclose encapsulation techniques which cause addition of amine components over a substantially instantaneous time period. It is the fast addition which is believed to facilitate agglomeration when applying those methods to the polyamide-polyurea microencapsulation of naturally-occurring pyrethrins. This invention overcomes these shortcomings and provides microencapsulated naturally-occurring pyrethrins which are at once free-flowing and non-agglomerating.

SUMMARY OF THE INVENTION

Microencapsulated naturally-occurring pyrethrins are formulated according to the practice of this invention through a microencapsulation process in which the nature of the reactants, the order of reactant addition, and the speed of reactant addition are carefully controlled. More particularly, polyamide-polyurea microcapsules containing naturally-occurring pyrethrins are formulated from isocyanate-acyl halide-amine reaction systems employing a modification of the Vandegaer interfactial polymerization process. This modification comprises the careful control of the rate of addition of amine component to the aqueous suspension of natural pyrethrin and isocyanate-acyl halide. More particularly, the amine is metered into the suspension at a rate so as to avoid local excesses of amine. This metering is believed to discourage reaction between naturally-occurring pyrethrins or associated impurities with the amine component by keeping the amine concentration low. It has been found necessary to maintain the free amine concentration at or below 1000 ppm, based upon the weight of the mixture. As a result, free-flowing, non-agglomerating microencapsulated naturally-occurring pyrethrins may be obtained which are suitable for numerous entomological uses.

DETAILED DESCRIPTION OF THE INVENTION

According to the practice of this invention, the naturally-occurring pyrethrin and the component or components of the first reactive species which comprises polyfunctional isocyanates and acyl halides, are mixed together to form an organic mixture with or without additional organic solvating agents. This mixture is then emulsified in an aqueous continuous phase under proper conditions of pH to form a dispersion of droplets of the pyrethrin-containing organic material. The second reactive species, which comprises the polyfunctional amine, is then metered into the suspension while it is under agitation. The performance of this step is critical to the practice of the present invention. It has been found that when the amine component is added to the suspension at a relatively rapid rate such as is disclosed by The Vandegaer and DeSavigny patents, such as that the concentration of free amine exceeds 1000 ppm, that tackiness and agglomeration occur to greater or lesser degrees, It has been found, however, that when the amine component is metered to the suspension at a relatively slow rate to keep the free amine concentration below 1000 ppm, the tackiness and agglomeration are avoided and a free-flowing microencapsulated naturally-occurring pyrethrin result. Thus, it has been found that the rate of addition of the amine complimentary reactant to the non-amine complimentary reactant in the dispersed water immiscible phase or suspension is a critical variable to the successful construction of useful microencapsulated naturally-occurring pyrethrins.

While the rate of addition of the amine-containing, second reactive component to the slurry or dispersion is best described by the results accomplished, i.e., by the accomplishment of free-flowing, non-tacky, non-agglomerating microencapsulated naturally-occurring pyrethrins, rather than by any quantitative measure of any absolute rate of component addition, certain quantitative measures of the proper rate of additiona may be set forth. Thus, in general, the amine-containing component will be metered in very slowly, preferably dropwise, to the slurry or dispersion. More particularly, the metered rate of amine addition should be such that a low concentration of amine component is maintained in the reaction vessel at below 1000 ppm until substantially all of the isocyanates and/or acyl halides have been reacted. Those skilled in the art will recognize that the time period over which amine addition may take place will vary depending upon reactants chosen, reaction scale and other variables. For a 20 mole scale, approximately 30 minutes will be usually sufficient for amine additions. While such objective, qualitative standards are helpful in determining proper rate of amine component addition, such rate is best determined individually for any given set of reaction parameters. Such determination is easily within the routine skill of those skilled in the art when apprised of the desired result. Thus, when advised that a free-flowing, non-tacky microencapsulated material will result from addition of amine component at a sufficiently slow rate while tackiness and agglomeration will result in greater or lesser degree upon selection of a rate of addition which is too high, those skilled in the art will easily be able to determine an appropriate rate of reaction for any given system. In any even, a suitable product will be prepared only if the free amine concentration is kept below about 1000 ppm.

The pyrethrins which are suitable for use in the embodiments of this invention may be any of the naturally-occurring, active constituents of pyrethrin and related plants. Thus, pyrethrin I, which is the pyrethrolone ester of chrysanthemummono-carboxylic acid, though to be most potent insecticide ingredient of pyrethrin flowers; of pyrethrin II, the pyrethrolone ester of chrysanthemumdicarboxylic acid, may be used. Additionally, numberous other pyrethrin flower-derived insecticidal agents such as cinerin I, and cinerin II, which are the 3-(2-butenyl)-4-methyl-2-oxo-3-cyclopenten-1-yl ester of chrysanthemummono-carboxylic acid, and dicarboxylic respectively, may be employed as may commercially available preparations of pyrethrin and related insecticides such as pyrethrin powder or extract. While this invention has been developed in order to overcome difficulties in microencapsulating naturally-occurring pyrethrins, it is also suitable for employment in the microencapsulation of synthetically-derived pyrethrins as well. Thus, permethrin, resmethrin, allethrin, cypermethrin, and other synthetic pyrethrins may be employed. It is also possible to employ mixtures of naturally-occurring pyrethrins and synthetic pyrethrins in one or more embodiments of this invention.

According to a preferred embodiment of the present invention, the pyrethrin insecticide or mixture may be "synergized" via techniques well-known to those skilled in the art. Thus, pyrethrins or mixtures of pyrethrins may be made more biologically active through the inclusion of synergizing agents such as piperonyl butoxide, 4-dodecyl-4'-dodecyloxy-2-hydroxybenzophenone, or other well-known synergizing agents. See in this regard, *Pyrethrum the Natural Insecticide,* Casida ed. (Academ, 1973) and *Pesticides,* Cremlyn, (Wiley, 1978), pp. 47–48. Several synergized pyrethrins including naturally-occurring pyrethrins are commercially available and are all suitable for employment in one or more of the embodiments of the invention. For convenience, it will be understood that the addition of synergizing agents will be a matter of choice for the practitioners of this invention and that the term "pyrethrin" will be understood to encompass formulations of pyrethrins which include synergizing agents as well.

According to this invention, microencapsulated naturally-occurring pyrethrins may be formulated employing cross-linked polyamide-polyureas as constituents of the capsule walls. For the practice of this method, the first reactive species, which is that species which is included with the pyrethrin in the suspended droplets, includes polyfunctional isocyanates and/or polyfunctional acyl halides. The second reactive species, which is introduced via the continuous liquid phase, comprises at least one amine.

Compositions suitable for use in the first reactive species include di-, tri-, and higher polyfunctional isocyanates together with polymers formed therefrom. Thus, isocyanates such as para-phenylene diisocyanate; meta-phenylene diisocyanate; naphthalene-1,5-diisocyanate; tetrachloro-m-phenylene diisocyanate; 2,4-toluene diisocyanate; 2,6-toluene diisocyanate; 4,4-diphenyl-diisocyanate; the dichloro diphenyl methane diisocyanates; bibenzyl diisocyanate; bitolylene diisocyanate; the diphenyl ester diisocyanates; the dimethyldiphenyl diisocyanates; the polymethylene polyphenyl isocyanates; triphenylmethane-4,4,4'-triisocyanate; isopropylbenzene alpha-diisocyanate; and the like may be employed as components of the first reactive species. Such polyfunctional isocyanates may be employed either in monomeric or polymeric form. For example, polymethylene polyphenyl isocyanate (known by its Upjohn Trademark "PAPI®")and similar polymers are preferred constituents of the first reactive species.

Examples of acyl halides suitable for use as components of the first reactive species include: sebacoyl chloride; ethylene-bis-chloroformate; phosgene; azelaoyl chloride; adipoly chloride; terephthaloyl chloride; dodecanedioic acid chloride; dimer acid chloride; 1,3-benzene flufonyl dichloride; trimesoyl chloride; 1,2,4,5-benzene tetra-acid chloride; 1,3,5-benzene trisulfonyl chloride; trimer acid chloride; citric acid chloride; and 1,3,5-benzene tris-chloroformate. According to this preferred procedure, the first reactive species is so formulated that the polymer resulting from the reaction of the first and second reactive species will be from about 10% to about 95% cross-linked. By this is meant that from about 10% to about 95% of the polymers of the polymeric cell wall are part of a three-dimensional polymer network. More preferably, from about 20% to about 50% cross-linking is employed and components of the first reactive species are preferably chosen so as to accomplish this goal. The amount of cross-linking present in the final polymeric product may be controlled through control of the degree of tri-, tetra-, and higher functionality in the isocyanate and acyl halide components of the first reactive species. Thus, an increase in the tri-, tetra-, and higher functional isocyanates and polyacyl halides increases the amount of cross-linking in the final product.

The amine which may be employed as the component of the second reactive species may be chosen from a wide variety of compounds having two or more amine functions. Examples of suitable amines include ethylene diamine; phenylene diamine; toluene diamine; hexamethylene diamine; hexamethylene triamine; diethylene triamine; triethylene tetramine; piperidine, 1,3,5-benzenetriamine trihydrochloride; 2,4,6-triaminotoluene trihydrochloride, tetraethylene pentamine; pentaethylene hexamine; polyethylene amine; 1,3,6-triaminonaphthalene; 3,4,5-triamino-1,2,4-triazole; melamine; 1,4,5,8-tetraminoanthraquinone; etc.; mixtures may, of course, also be employed.

The processes for the formulation of microencapsulated naturally-occurring pyrethrins may profitably employ numerous species in addition to the pyrethrins and the capsule wall components. Thus, formulations according to this invention may include clays, pigments, viscosity modifiers, polymers, gelatins, suspension agents, dyes, anti-foaming agents, preservative, anti-oxidants, U.V. stabilizers, and numerous other families of materials as will occur to those skilled in the art. It is particularly helpful to incorporate anti-oxidants and U.V. stabilizers along with the pyrethrins chosen for microencapsulation. The addition of these agents serves further to protect the pyrethrins from degradation and, thus, to improve the overall persistency of insecticidal compositions formulated hereby.

Those skilled in the art will appreciate that the average thickness of capsule walls which may be employed for the microencapsulation process of this invention may be varied by varying the relative amounts of the material to the encapsulated as compared to the encapsulation compositions. Those skilled in the art will similarly appreciate that the relative thickness of the capsule wall as well as the degree of cross-linking present in the polymer constituting such capsule wall affect the rate of diffusion of the pyrethrin insecticide through the wall and influence both the persistency of the insecticide and its potency at any given point in time. As previously mentioned, control of the polyfunctionality of the isocyanates and/or acyl halides will vary the amount of cross-linking in the resulting capsule walls. Thus, one may monitor the degree of dispersion of the material to be encapsulated, may control the amount of agitation, and may add, on a controlled basis, emulsifying agents to the aqueous phase all as well-understood by those skilled in the art. The microcapsule wall thickness may be controlled by the quantity of the reactive intermediates available for polymer formation. While the amount of insecticide expressed as a weight ratio to the amount of encapsulation composition may vary widely from about 2:1 to about 10:1, a weight ratio of approximately 5:1 is preferred for many applications. Those skilled in the art, following the general guidelines expressed above and in view of the Vandegaer and DeSavigny references which have been incorporated herein by reference, will easily be able to formulate microencapsulated naturally-occurring insecticides according to the present invention having any desired weight ratio of insecticide to polymer.

The microencapsulated naturally-occurring insecticides may be employed in various ways. Thus, aqueous slurries of the insecticide may be employed for spraying purposes on crops or otherwise for insect control. One preferred use for the microencapsulated naturally-occurring insecticides of this invention is discussed in the related application Ser. No. 177,212, filed Aug. 11, 1980, and now abandoned entitled "Entomologically Active Coating Materials for Comestible Packaging". Thus, the microencapsulated products produced according to this invention may be included in various coating formulations and used to coat various packaging materials suitable for the enclosure of comestibles. Such coated packaging material has been shown to have a significantly greater persistency against attack from insects than do coating materials employing unencapsulated pyrethrins or packaging materials which have been sprayed with native solutions of unencapsulated pyrethrins. Attempts to formuate microencapsulated naturally-occurring pyrethrins according to the methods of Vandegaer, or according to processes wherein the rate of addition of amine component has not been controlled, and, accordingly, wherein tackiness or agglomeration of the resulting microcapsules has been evidenced, has resulted in insecticides which are relatively unsuitable for use in coating materials. Thus, the present invention fills a long-felt need for microencapsulated naturally-occurring pyrethrins for use in coating compositions for comestible packaging materials and for other purposes.

EXAMPLE 1

Comparison Example

An organic mixture comprising 50 g of synergized natural pyrethrin (6.1% active with 10-fold amount of piperonyl butoxide), 2.37 g of sebacoyl chloride (95%) and 2.65 g of PAPI (polymethylene polyphenylisocynante trademark of the Upjohn Company) was emulsified in 140 ml of 0.5% aqueous solution of Gelvatol (a partially-hydrolyzed polyvinyl alcohol available from the Monsanto Co.). This dispersion was accomplished in a 400 ml glass vessel fitted with a stopcock valve at its base employing a Kraft dispersator at setting #6. After 30 seconds of emulsification, the dispersion was transferred through the stopcock onto a 400 ml beaker. To this dispersion was added all at once an aqueous solution containing 1.19 g of ethylene diamine, 1.6 g of 50% NaOH solution and 10 g of water. Free amine concentration of nearly 5000 ppm decreased as the reaction took place, but not before the microcapsules thus formed agglomerated immediately upon formation and could not be sieved through a #50 mesh screen. The product is not suitable for the formulation of insecticidal compositions and cannot be employed as a constituent of coatings of packaging materials for comestibles.

EXAMPLE 2

The organic mixture of Example 1 was emulsified in a 1% aqueous solution of Elvanol using a dispersator setting of #6.5 for one minute. The resulting dispersion was transferred to a 400 ml beaker and an aqueous solution of 1.6 g of 50% of NaOH in 10 ml water was added with stirring. 1.19 g of ethylene diamine was added dropwise over a period of at least 30 minutes, while the emulsion was being stirred mechanically whereby the unreacted amine concentration was no more than 400 ppm. After further stirring for one hour, the capsule slurry was neutralized to approximately neutral pH with HCl. The slurry could easily pass through a #50 sieve and microscopic examination disclosed normal, spherical capsules of microencapsulated synergized natural pyrethrin having average capsule diameters from about 30 microns to about 35 microns.

EXAMPLE 3

The procedure of Example 2 was repeated except that an additional 1.36 g of diethylenetriamine was mixed with the ethylene diamine in aqueous solution. The mixed amines were added dropwise as in Example 2, keeping the unreacted amine concentration at or below 950 ppm. A good encapsulation was obtained without agglomeration and the slurry easily passed through a #50 sieve.

EXAMPLE 4

The encapsulation of synergized natural pyrethrin was performed exactly as in Example 2 except that an antioxidant (2,6-di-tetra-butyl-4-methylphenol, 0.0346 g), and a U.V. stabilizer, (TINUVIN 328, trademark of Ciba-Geigy, 334 g), were added to the organic mixture. Maximum unreacted amne was kept below 1000 ppm, based upon the mixture weight. The slurry thus prepared was calculated to have approximately 1.5% active pyrethrin based on slurry weight and was found to be well-formed and non-agglomerating.

EXAMPLE 5

The process of Example 2 was reproduced on a ten-fold scale. An organic mix comprising 500 g of synergized natural pyrethrin (6.0% active with 10-fold amount of piperonyl butoxide), 26.5 PAPI, and 23.7 g of sebacoyl chloride was emulsified in 1.4 liters of 0.5% aqueous solution of Elvanol. The dispersion was performed in a 3 liter baffled resin flask employing a Kraft dispersator for 30 seconds at #6 setting. The dispersion was maintained with a regular stirrer while 16 g of a 50% NaOH solution was added. An aqueous mix comprising 25 ml water, 11.9 g ethylene diamine and 13.6 g diethylene triamine was added slowly at the rate of approximately one drop per second for approximately 50 seconds at which time the addition rate was increased to approximately two drops per second to completion. This rate maintained the amine concentration at levels below about 1000 ppm during the entire amine addition step. The reaction mixture was neutralized with dilute hydrochloric acid to a pH of approximately 6 to 6.5. The slurry passed through a #50 sieve and was disclosed to be a regular, free-flowing, and roughly spherical. The product was analyzed to contain approximately 1.7% of active natural pyrethrin and to have an average capsule size of approximately 34 microns. To improve the suspension stability of the capsules, 0.35% by weight of Kelzan (a xanthan gum produced by the Kelco Company) was added. This thickened dispersion was found to have excellent insecticidal properties and to display good persistency.

EXAMPLE 6

The effectiveness and persistency of the microencapsulated natural pyrethrins according to this invention is demonstrated by this example.

Cardboard cartons were sprayed with the designated insecticidal compositions and infested with houseflies after designated periods. The percent of mortality of the houseflies was determined 24 hours after the flies were placed on the treated surface. The data is presented in the following table:

TABLE I

| SAMPLE | DAY % - KILL | | | | | | |
|---|---|---|---|---|---|---|---|
| | 1 | 3 | 7 | 10 | 15 | 22 | 29 |
| Control - No Active Ingredient | 13 | 0 | 1 | 0 | 0 | 0 | 0 |
| Synergized Natural Pyrethrin (unencapsulated, 6.0% active with 10-fold piperonyl butoxide) | 100 | 72 | 6 | 13 | 0 | 0 | 0 |
| Synthetic Pyrethrin (Resmethrin - S.B. Penick Co.) | 84 | 22 | 0 | 6 | 0 | 0 | 0 |
| Example 2 material | 100 | 100 | 100 | 100 | 99 | 100 | 100 |

The superiority of the microencapsulated natural pyrethrins over either unencapsulated natural pyrethrin or unencapsulated Resmethrin is demonstrated. An effort to spray the material of Example 1 was made, but was unsuccessful, and the effectiveness could not be evaluated.

I claim:

1. A process for microencapsulating naturally-occurring pyrethrins with a polyamide-polyurea shell by interfacial condensation of complementary, organic, di- or polyfunctional polycondensate-forming intermediates reacting to form a polyamide-polyurea condensate, comprising (a) forming a suspension in an aqueous emulsion of
      (i) the naturally-occurring pyrethrin to be microencapsulated;
      (ii) at least one isocyanate; and
      (iii) at least one acyl halide; with at least one of said isocyanate or said acyl halide being polyfunctional; and then
   (b) adding to the aqueous emulsion of (a), with agitation under reaction conditions, at least one amine at such a rate as to maintain the concentration of unreacted amine below 1000 parts per million of total weight of (a) and (b), to provide substantially non-agglomerated, free-flowing microcapsules of said pyrethrin having a shell of polyamide-polyurea.

2. The process as defined in claim 1 wherein in (a) (i) said pyrethrin has been admixed with at least one synthetic pyrethrin.

3. The process as defined in claim 2 wherein in (a) (iii) said acyl halide is selected from the group of acyl halides consisting essentially of sebacoyl chloride; ethylene-bis-chloroformate; phosgen; azelaoyl chloride; adipoyl chloride; terephthaloyl chloride; dodecanedioic acid chloride; dimer acid chloride; 1,3-benzene disulfonyl chloride; trimesoyl chloride; 1,2,4,5-benzene tetra-acid chloride; 1,3,5-benzene trisulfonyl chloride; trimer acid chloride; citric acid chloride; and 1,3,5-benzene tris-chloroformate.

4. The process as defined in claim 3 wherein in (b) said amine is selected from the group of amines consisting essentially of ethylene diamine; phenylene diamine; toluene diamine; hexamethylene diamine; diethylene triamine; triethylene tetramine; piperidine; 1,3,5-benzenetriamine trihydrochloride; 2,4,6-triaminotoluene trihydrochloride; tetraethylene pentamine; pentaethylene hexamine; polyethylene amine; 1,3,6-triaminonaphthalene; 3,4,5-triamino-1,2,4-triazole; melamine; and 1,4,5,8-tetraaminoanthraquinone.

5. The process as defined in claim 1 wherein in (a) (ii) said isocyanate is selected from the group of isocyanates consisting essentially of para-phenylene diisocyanate; meta-phenylene diisocyanate; naphthalene-1,5-diisocyanate; tetrachloro-m-phenylene diisocyanate; 2,4-toluene diisocyanate; 2,6-toluene diisocyanate; 4,4-diphenyl-diisocyanate; dichloro diphenyl methane diisocyanate; bibenzyl diisocyanate; bitolylene diisocyanate; diphenyl ester diisocyanate; dimethyldiphenyl diisocyanate; polymethylene polyphenyl isocyanate; triphenylmethane-4,4,4'-triisocyanate; and isopropylbenzene alpha-diisocyanate.

6. The process of claim 1 wherein said amine is maintained below a concentration of 400 ppm.

7. A persistent, naturally-occurring pyrethrin insecticide which has been microencapsulated according to the process of claim 1.

8. The insecticide of claim 7 wherein said pyrethrin has been synergized.

9. The insecticide of claim 7 wherein said pyrethrin has been admixed with at least one synthetic pyrethrin.

10. The insecticide of claim 9 wherein said pyrethrin has been synergized.

* * * * *